Figure 1A:
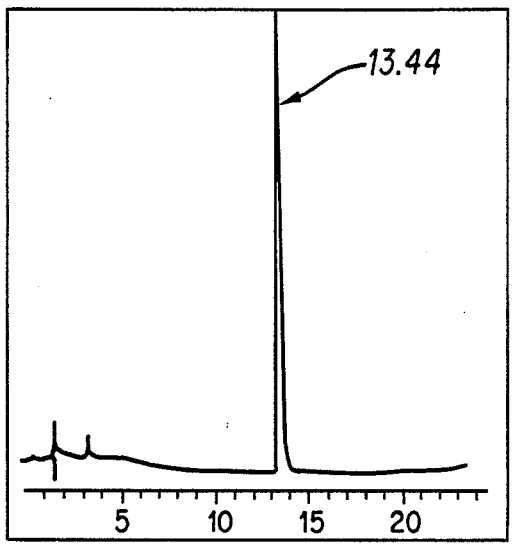

| United States Patent [19] | [11] Patent Number: 4,960,868 |
| Canosi et al. | [45] Date of Patent: Oct. 2, 1990 |

[54] METHOD OF CLEAVAGE AT METHIONINE OF POLYPEPTIDES

[75] Inventors: Umberto Canosi; Gabriele De Fazio; Stefano Villa, all of Rome, Italy

[73] Assignee: Istituto di Ricerca Cesare Serono SpA, Ardea, Italy

[21] Appl. No.: 310,426

[22] Filed: Feb. 13, 1989

[30] Foreign Application Priority Data

Feb. 17, 1988 [IT] Italy ................. 47643 A/88

[51] Int. Cl.$^5$ ............... C07K 1/12; C07K 3/10
[52] U.S. Cl. .................... 530/389; 530/303; 530/311; 530/324; 530/333; 530/345; 530/399; 530/409
[58] Field of Search ............ 530/345, 389, 311, 333, 530/303, 399, 409, 324

[56] References Cited

U.S. PATENT DOCUMENTS 4,476,049 10/1984 Kung .................. 530/351
4,721,673 1/1988 Uren et al. .......... 435/183

OTHER PUBLICATIONS

White et al., *Principles of Biochemistry*, 1978, p. 75.
Gross et al., *J. Am. Chem. Soc.*, 1961, vol. 83, pp. 1510–1511.

*Primary Examiner*—Lester L. Lee
*Assistant Examiner*—Stephen B. Maebius
*Attorney, Agent, or Firm*—Stephan P. Williams

[57] ABSTRACT

A method for cleaving polypeptides at their methionine residue(s) by mean of reaction with cyanogen bromide wherein a solution of guanidium chloride into hydrochloric acid is employed as reaction medium.

11 Claims, 2 Drawing Sheets

METHOD OF CLEAVAGE AT METHIONINE OF POLYPEPTIDES

This invention relates to a method for cleaving polypeptides at their methionine residue(s) through the use of a solution of guanidine in hydrochloric acid together with cyanogen bromide.

Various peptides of pharmacological interest, not containing the methionine aminoacid, such as somatostatin (K. Itakura et al., Science 198 1056–1063, 1977), insulin (Goeddel et al., Proc. Natl. Acad. Sci. USA 76, 106, 1979), EGF analogs (Sumi et al., J. Biotechnology 2, 59–74, 1985), or GRF analogs (Kempe et al., Bio-Technology 4, 565–568, 1986) have been produced by DNA recombinant techniques from microbial, e.g. bacterial cells. The genes encoding said peptides have been cloned in plasmid vectors (carriers) in such a way to express hybrid proteins. These hybrid proteins consist of a polypeptidic sequence, preferably of bacterial origin, at the amino-terminal portion, joined to the peptide of pharmacological interest, at the carboxy-terminal portion. The two portions are separated by a methionine.

The separation of the two moieties which compose the hybrid protein is achieved by reaction with cyanogen bromide (CNBr), a chemical compound which specifically cleaves a polypeptide chain with a high specificity at the carboxyl group of methionine residue(s). The literature reports that the cleavage reaction with CNBr is generally performed in the presence of 70% formic acid (Meth. in Enzymol. 11, 238, 1967). 70% formic acid represents a good protein-solubilizing means. Furthermore, under suitable conditions, whole cells of E. coli can be easily disrupted by such solution (Itakura et al., Science 198, 1056, 1977). This is of particular advantage when dealing with proteins produced via rec-DNA technology.

Whilst this method has a preferred application for the cleavage of hybrid polypeptides whose peptide fraction of biological interest does not contain the methionine amino acid, it is also applied to the cleavage of polypeptides, irrespective of their origin, containing methionine amino acids. For instance, the selectivity of the cleavage of the carboxyl group of methionine with CNBr is such that the method has been widely utilized also in protein sequencing operations.

However, it has been found that such method may present some drawbacks if the protein molecule to be prepared contains inter- and/or intra-molecular disulfide bonds. Formic acid has reducing properties (The Merck Index, 10th Ed., pag. 605, 1983) that may affect the production yield of peptides containing inter- and/or intra-molecular disulfide bonds. In fact, these bonds may be reduced during the CNBr reaction in presence of 70% formic acid and not properly reoxidized during the further purification of the peptides, generating aspecific intermolecular (between two polypeptides chains) and/or intramolecular (within the same polypeptide chain) disulfide bonds which were not present in the starting molecule.

A first object of this invention is to provide a new process for the cleavage of polypeptides at the methionine residue(s). A second object of the invention is to provide a method permitting to recover in a substantially quantitative way the peptide molecules, released b cleavage at the Met residue(s) by CNBr, without reducing the disulfide bonds.

The present invention is based upon the use of a solution of Guanidine hydrochloride (GdmCl) (often called guanidium chloride) in the presence of suitable amounts of hydrochloric acid as a reaction mean for the cleavage by CNBr at the methionine residue(s) of a polypeptide Such a reaction mean allows both the dissolution of purified proteins and the disruption and homogenization of whole cells expressing a desired polypeptide or an intermediate thereof, permitting in both cases the cleaving reaction at the methionine of the polypeptide by CNBr to take place.

The method according to the present invention may be applied for cleaving recombinant heterologous hybrid polypeptides with release of the interesting peptide. The method may also be applied to assign the correct positions of disulfide bonds in protein molecules.

We have found that the solution of Guanidine hydrochloride into hydrochloric acid does not possess any reducing activity when used in a method according to the present invention. Therefore, any possible disulfide bonds of the proteins are not altered. Furthermore, said solution has a dissolving capacity better than that of 70% formic acid, thus permitting a significant reduction of the reaction volumes, both when using a purified protein and when intact microbial, e.g. bacterial, cells are employed In a preferred embodiment the cells are prepared by rec-DNA.

Guanidine hydrochloride is preferably utilized at the 6 M concentration, even if lower concentrations can be utilised in the process of the present invention. The concentration of guanidine hydrochloride must, anyway, be such to permit a good solubilisation of the proteins and/or whole cells to be treated.

The molar concentration of the hydrochloric acid in the final solution is normally comprised between 0.1 and 1 M. This range is consistent with the requirements of an efficient solubilisation and a satisfactory stability of the proteins in the reaction medium. The invention is described with particular reference to the preparation of cyclic somatostatine from a hybrid polypeptide, designated as TrpE-Met-SS14, obtained through the procedures described in the European patent application EP-A-160190. Other practical examples to which the method of the present invention is applicable are the preparation of the Epidermal Growth Factor (EGF) through the cleavage, by means of CNBr, of a hybrid polypeptide with beta-galactosidase (J. of Biotechnology 2, 59, 1985); the preparation of human proinsulin from a precursor expressed in E. coli, for instance according to the method described in the European patent Application No. EP-A-55945; and any similar situation in which the polypeptide that one wants to isolate contains at least one methionine residue, and preferably inter- and/or intra-molecular disulfide bonds, since these bonds are sensitive to reducing agents.

Preliminary experiments performed with somatostatin or porcine insulin have demonstrated the reducing effect of formic acid. It was then found that by replacing formic acid with guanidium chloride dissolved into HCl, cleavage at the methionine residue(s) still occurred whilst no reduction of the disulfide bonds took place.

The analysis of the cyclic somatostatin has been performed by means of HPLC or by the radioimmunoassay method. In this case, for the cyclic somatostatin, polyspecificity for the cyclic somatostatin and not-recognizing the linear molecule. The insulin analysis has been performed by means of HPLC.

Figure 1B:
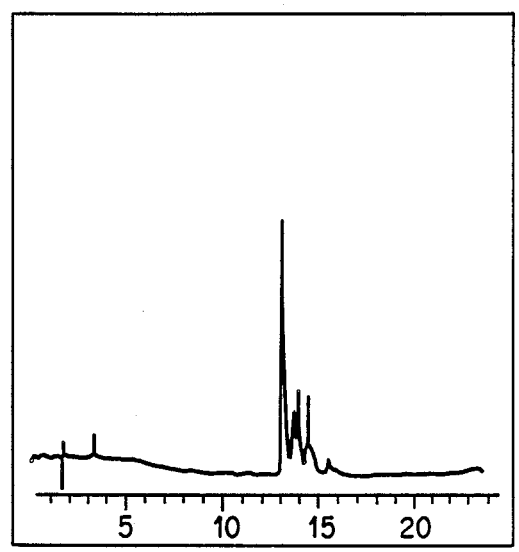
Figure 1C:
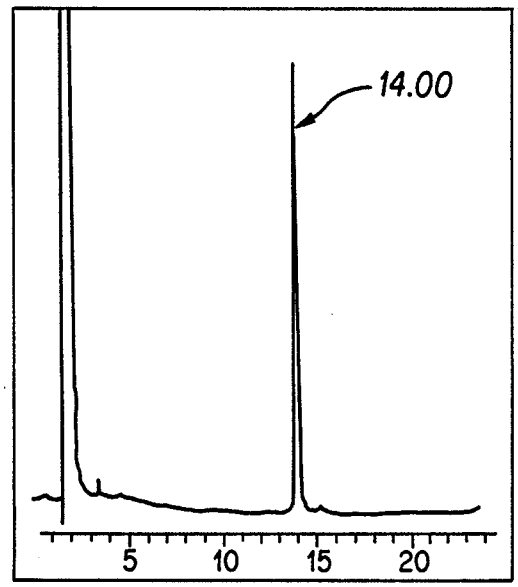
Figure 1D:
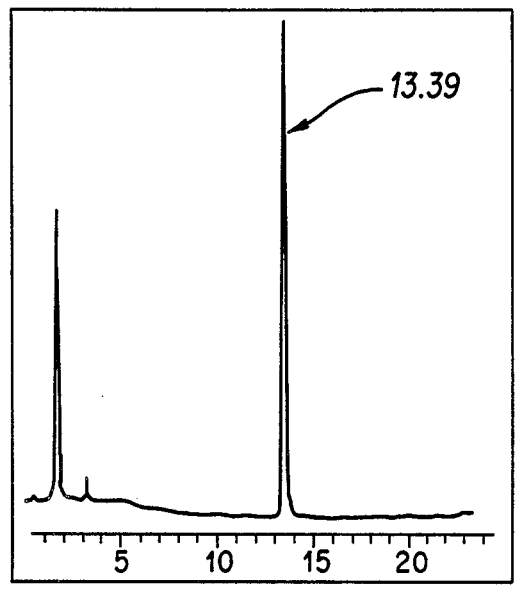

The preliminary tests are illustrated in the Figures, wherein:

FIG. 1 shows the HPLC chromatograms of:
(A) cyclic SS14;
(B) SS14 treated with 70% formic acid: it is observed a reduction of the peak corresponding to cyclic SS14 and the appearance of other peaks of linear SS14 and of various polymerized SS14;
(C) the material resulting from (B), further treated with DDT: the remaining cyclic SS14 and the various polymerized forms resulting from (B) are also converted into linear SS14;
(D) cyclic SS14, treated with 6 M guanidine in 0.2 M HCl: the whole SS14 maintains the starting cyclic form.

Figure 2A:
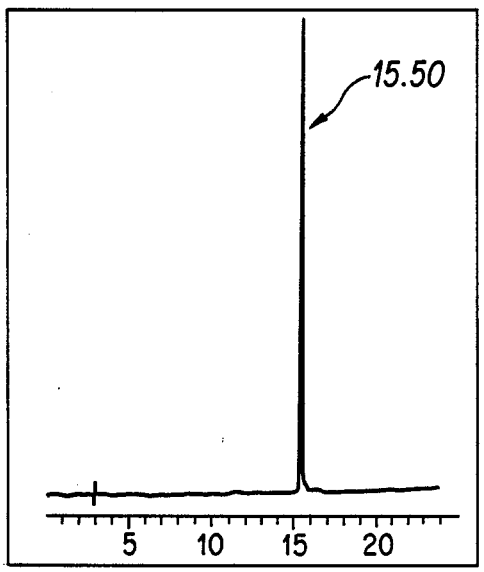
Figure 2B:
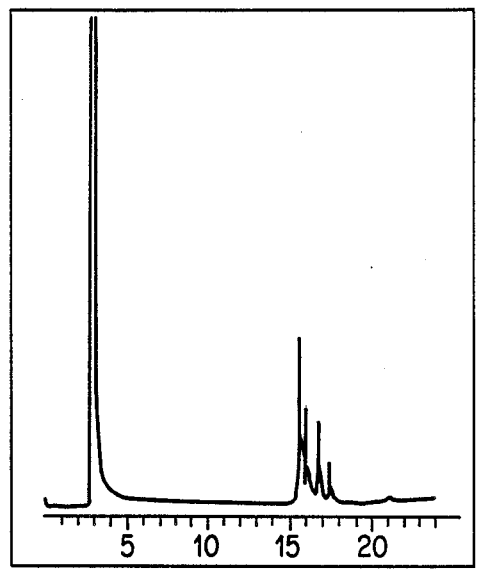
Figure 2C:
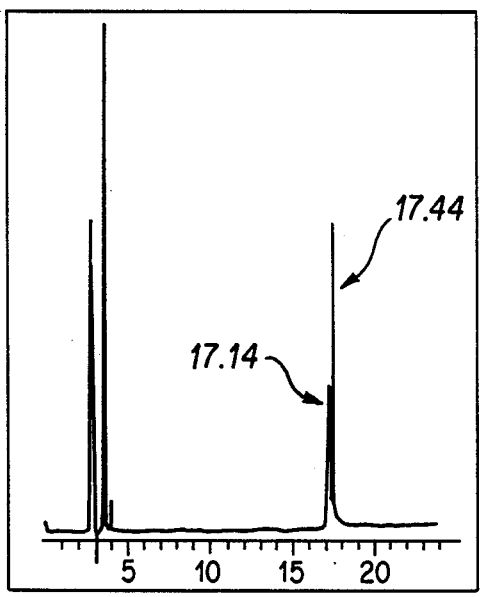
Figure 2D:
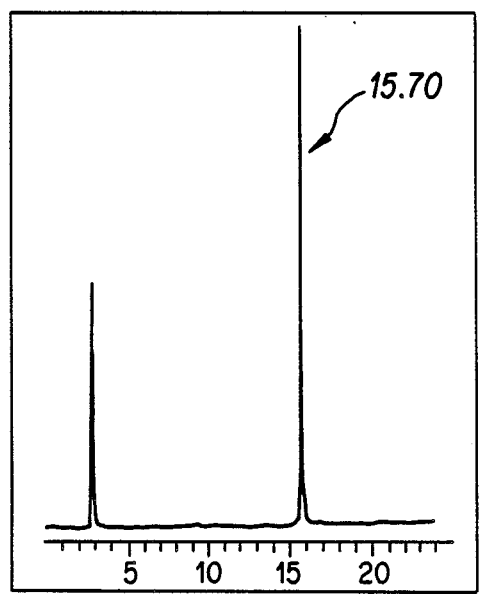

FIG. 2 shows the HPLC chromatograms of:
(A) standard a-b insulin;
(B) a-b insulin treated with 70% formic acid: it is observed a reduction of the peak corresponding to the standard a-b insulin, as well as the appearance of other peaks;
(C) the material resulting from (B) is further treated with DDT: the whole a-b insulin is converted to single a and b linear insulin chains;
(D) standard a-b insulin treated with 6 M Guanidium chloride in 0.2 M HCl: the whole insulin remains in the complex a-b form.

PRELIMINARY TESTS (1) 100 mcg of cylic SS14 (synthetic somatostatin, Stilamin ®, Serono) are treated with 1 ml of 70% formic acid. After 18 hours incubation at room temperature, the solution is analyzed by HPLC. A 70% reduction has been observed of SS14 together with the appearance of various polluting peaks (FIG. 1 A, B). After lyophilization, the mixture has been treated with an excess of dithiotreitol (DDT) (a strong reducing agent) at pH 8.5 for 2 hours at 37° C. A single peak is obtained (100% of the starting amount) of linear Somatostatin (FIG. 1 C). This substantiates the finding that 70% formic acid reduces, (although not in a quantitative way), the disulfide bond of SS14 with formation of a mixture of cyclic SS14, linear SS14 and various polymerized forms. This mixture, when treated with a strong reducing agent as DDT, is quantitatively converted into linear Somatostatin. In a similar experiment, performed by using, instead of 70% formic acid, a solution of 6 M guanidine hydrochloride into 0.2 M HCl, after 18 hours incubation at room temperature, no reduction was observed of cylic Somatostatin at a HPLC test (FIG. 1 D).

(2) 100 mcg porcine insulin are treated with 100 microliters of 70% formic acid. After 18 hours incubation at room temperature the solution is analyzed by HPLC. A reduction is observed of the insulin peak, as well as the appearance of other remarkable contaminating peaks (FIG. 2 A, B). Thus formic acid strongly affects the porcine insuline by partially reducing its disulfide bonds. After lyophilization, the mixture has been treated with an excess of dithiotreitol (DDT) at pH 8.5 during 2 hours at 37° C. Only two peaks are obtained, both representing, qualitatively and quantitatively, the two single a and b linear insulin chains. In a similar experiment, effected by using, instead of 70% formic acid, a solution of 6 M Guanidine hydrochloride into 0.1 M HCl, after 18 hours incubation at room temperature, no reduction of the concentration of native insulin by HPLC assay was noticed (FIG. 2 D).

The method which is the object of the present invention has been applied both to the hybrid protein TrpE-SS14 partially purified, and to a bacterial cell suspension containing the same.

The experimental results are illustrated in the following examples. Example 1 illustrates the application of the method of the present invention to the cleavage of the partially purified TrpE-SS14 hybrid insulin, for instance as obtained by the process which is described in the European Patent Application EP-A-160190. Example 2 illustrates the application of the method of the present invention to the processing of whole E. coli cells grown under conditions of TrpE-SS14 protein expression.

EXAMPLE 1

(A) Preparation of the lysate:

E. coil cells were grown as described in EP-A-160190 for the expression of the TrpE-Met-SS14 polypeptide. 100 g of these cells were re-suspended in 500 ml of 0.2 M Tris-HCl, pH 7.6; 0.2 M NaCl, 0.01 M Mg acetate and 5% glycerol, and disintegrated at 4° C. by the Dyno Mill KDL disintegrator (WAB, Switzerland) which employs glass microspheres. After homogenization the lysed cell suspension was filtered through a piece of gauze to separate the glass microspheres and the cellular debris. The TrpE-Met-SS14 protein is insoluble and tends to precipitate spontaneously; however, a quicker precipitation is achieved through the addition of 10% ammonium sulphate. After the addition of the salt, the mixture is stirred, and divided into 10 ml samples for the next treatments.

(B) Treatment by formic acid/CNBr:

A 10 ml sample is centrifuged at 10.000 g for 15 minutes and the pelletted proteins are re-suspended with 10 ml of 70% formic acid containing 240 mg of CNBr. The reaction mixture is then incubated at 4° C. during 18 hours, then is centrifuged to remove insoluble matters, and the supernatant is collected for the titration of the present cyclic SS14. Analysis by HPLC shows the presence of 14 mcg/ml of cyclic SS14.

(C) Treatment by Guanidine-HCl/CNBr:

A 10 ml sample is centrifuged at 10.000 g for 15 minutes and the pelletted proteins are re-suspended with 10 ml of 6 M Guanidine in 0.2 M HCl containing 240 mg di CNBr. The reaction mixture is incubated at 4° C. for 18 hours, then is centrifuged to remove insoluble matters, and the supernatant is collected for titration of the cyclic SS14 present. The HPLC analysis shows the presence of 47 mcg/ml of cyclic SS14.

The above reported experimental results show that the substitution of 70% formic acid with Guanidine-HCl, according to the method of the present invention, permits a very significant increase (47/14) of the cyclic SS14 obtained through cleavage at Met with CNBr.

EXAMPLE 2

(A) 160 mg of E. coli cells, obtained after centrifugation of 10 ml of a bacterial culture containing a TrpE-Met-SS14 hybrid polypeptide (see European patent Application EP-A-160190), are re-suspended in 10 ml of 70% formic acid containing 26.6 mg of CNBr and stirred for 1 minute in order to achieve a good solubilization of the cells. After 18 hours incubation at room temperature, the reaction mixture is centrifuged, and the supernatant is collected in order to permit the titration of the cyclic SS14 present. The titration, performed by RIA (Radio Immuno Assay), shows the presence of 10.8 mcg of cyclic SS14 per ml of culture.

(B1) 160 mcg of *E. coli* cells obtained after centrifugation of 10 ml of a bacterial culture containing a TrpE-Met-SS14 hybrid polypeptide (see EP-A-160190) are re-suspended in 10 ml of 6 M Guanidine in 1 M HCl. 26.6 mg of CNBr are added, the mixture is stirred for 1 minute in order to solubilize the cells and the reaction mixture is incubated for 18 hours at room temperature. The cellular debris are removed by mean of centrifugation, and the cyclic SS14, titrated by the RIA method, is 27.57 mcg per ml of culture.

(B2) 160 mcg of cells, obtained after centrifugation of 10 ml of a bacterial culture containing a TrpE-Met-SS14 hybrid polypeptide (see EP-A-160190), are re-suspended in 10 ml of 6 M guanidine in 0.2 M HCl. 26.6 mg of CNBr are added, the mixture is stirred for 1 minute, and the reaction mixture is incubated for 18 hours at room temperature. After removal of cellular debris by centrifugation, the Somatostatin released by reaction with CNBr is titrated by the RIA method, and is 24.8 mcg per ml of culture.

(B3) 160 mcg of cells, obtained after centrifugation of 10 ml of a bacterial culture containing a TrpE-Met-SS14 hybrid polypeptide (see EP-A-160190), are re-suspended in 5 ml of 6 M Guanidine in 1 M HCl. 26.6 mg of CNBr are added, the mixture is stirred for 1 minute in order to solubilize the cells and the mixture is incubated for 18 hours at room temperature. The cellular debris are removed by centrifugation, and the cyclic SS14, titrated by the RIA method, is 26.6 mcg per ml of culture.

(B4) 160 mcg of cells, obtained after centrifugation of 10 ml of a bacterial culture containing a TrpE-Met-SS14 hybrid polypeptide (see EP-A-160190) are re-suspended in 5 ml of 6 M Guanidine in 0.2 M HCl. 26.6 mg of CNBr are added, the mixture is stirred for 1 minute in order to solubilize the cells, and the mixture is incubated for 18 hours at room temperature.

The cellular debris are removed by centrifugation and the cyclic SS14, titrated by the RIA method, results to be 21.25 mcg per ml of culture.

The results of Example 2 are summarized in the following Table which lists the amounts of cyclic SS14 released by reaction with CNBr in the presence of either 70% formic acid or of the various solutions of Guanidine +HCl.

TABLE

Effect of Formic Acid and Guanidine Hydrochloride on Cyclic Somatostatin Production

| Cell lysis mixture | Reaction Volume (ml) | Cyclic SS14 (mcg/ml)* | B/A |
|---|---|---|---|
| (A) 70% Formic acid | 10 | 10.8 | — |
| (B1) 6 M Guanidine in 1 M HCl | 10 | 27.57 | 2.55 |
| (B2) 6 M Guanidine in 0.2 M HCl | 10 | 24.8 | 2.29 |
| (B3) 6 M Guanidine in 1 M HCl | 5 | 26.5 | 2.45 |
| (B4) 6 M Guanidine in 0.2 M HCl | 5 | 21.25 | 1.97 |

*The concentrations are relative to 1 ml of culture.

The analysis of the above results shows that, according to the method of the present invention a recovery of cyclic SS14 is achieved which is significantly higher than that obtained by the conventional method employing 70% formic acid. Furthermore, the increase of the cyclic SS14 yield remains significant even if the volume of the reaction solvent is halved or if the concentration of the hydrochloric acid into which the Guanidine has been dissolved is reduced.

Although the present invention has been illustrated by means of specific Examples, it is understood that variants may be introduced in the applications herein described, without departing from the spirit and the scope of the invention itself.

We claim:

1. In a method for the cleavage of a polypeptide at methionine which comprises reacting said polypeptide with cyanogen bromide, the improvement wherein said reaction is conducted in a solution of guanidine hydrochloride and hydrochloric acid.

2. A method according to claim 1 wherein the polypeptide is a heterologous hybrid polypeptide containing a peptide of interest joined to the carboxyl portion of methionine and cleavage results in the release of the peptide of interest.

3. A method according to claim 1 or 2 wherein the polypeptide contains inter- and/or intra-molecular disulfide bonds.

4. A method according to claim 3 wherein the reaction is performed on whole cells expressing said polypeptide.

5. A method according to claim 2 wherein said solution comprises 6 M guanidine dissolved in 0.1 to 1 M hydrochloric acid.

6. A method according to claim 5 wherein said polypeptide contains the amino acid sequence of Somatostatin.

7. A method according to claim 5 wherein said polypeptide contains the amino acid sequence of Pro-insulin.

8. A method according to claim 5 wherein said polypeptide contains the amino acid sequence of Epidermal Growth Factor.

9. A method according to claim 6, 7 or 8 wherein reaction is performed on whole *E. Coli* cells expressing said polypeptide.

10. A method according to claim 1 wherein said solution comprises 6 M guanidine dissolved in 0.1 to 1 M hydrochloric acid.

11. A method according to claim 1 wherein said polypeptide contains an amino acid sequence selected from Somatostatin, Pro - insulin and Epidermal Growth Factor.

* * * * *